United States Patent
Zweig

(10) Patent No.: US 8,190,374 B2
(45) Date of Patent: *May 29, 2012

(54) METHOD AND DEVICE TO DETECT THERAPEUTIC PROTEIN IMMUNOGENICITY

(76) Inventor: Stephen Eliot Zweig, Los Gatos, CA (US)

( * ) Notice: Subject to any disclaimer, the term of this patent is extended or adjusted under 35 U.S.C. 154(b) by 1287 days.

This patent is subject to a terminal disclaimer.

(21) Appl. No.: 11/754,363

(22) Filed: May 28, 2007

(65) Prior Publication Data

US 2007/0243621 A1    Oct. 18, 2007

Related U.S. Application Data

(63) Continuation-in-part of application No. 10/747,926, filed on Dec. 29, 2003, now abandoned, which is a continuation-in-part of application No. 11/515,310, filed on Sep. 1, 2006, now Pat. No. 7,564,364, which is a continuation-in-part of application No. 10/824,709, filed on Apr. 14, 2004, now Pat. No. 7,102,526, which is a continuation-in-part of application No. 10/634,297, filed on Aug. 5, 2003, now Pat. No. 6,950,028.

(60) Provisional application No. 60/465,434, filed on Apr. 25, 2003, provisional application No. 60/496,358, filed on Aug. 18, 2003, provisional application No. 60/502,834, filed on Sep. 12, 2003, provisional application No. 60/506,814, filed on Sep. 26, 2003.

(51) Int. Cl.
*G01N 33/48* (2006.01)
(52) U.S. Cl. ......................................... 702/20
(58) Field of Classification Search ...................... 702/20
See application file for complete search history.

(56) References Cited

U.S. PATENT DOCUMENTS

| | | | |
|---|---|---|---|
| 4,277,974 A | 7/1981 | Karr et al. | |
| 4,389,217 A | 6/1983 | Baughman et al. | |
| 5,313,848 A | 5/1994 | Satin et al. | |
| 5,667,303 A | 9/1997 | Arens et al. | |
| RE36,200 E | 4/1999 | Berrian et al. | |
| 6,217,213 B1 | 4/2001 | Curry et al. | |
| 6,544,925 B1 | 4/2003 | Prusik et al. | |
| 6,629,057 B2 | 9/2003 | Zweig et al. | |
| 2004/0010233 A1* | 1/2004 | Hjertman et al. | 604/187 |

FOREIGN PATENT DOCUMENTS

WO    WO0125472 A1    4/2001

OTHER PUBLICATIONS

Rosenberg, Immunogenicity of Biological Therapeutics, A Hierarchy of Concerns, Dev. Biol. Basel, Karger 2003, vol. 112, pp. 15-21.
Chamberlain, "Immunogenicity of Therapeutic Proteins", The Regulatory Review 5: Aug. 5, 2002, pp. 4-9.
Hochuli, "Interferon immunogenicity: Technical Evaluation of Interferon 2", J. Interferon and Cytokine Res. 17 supplement 1: S15-S21, 1997.
DePaolis et. al. "Characterization of erythropoietin dimerization", J Pharm Sci. Nov. 1995; 84(11): 1280-4.
Haselbeck, "Epoetins: differences and their relevance to immunogenicity", Current Medical Research and Opinions 19(5), p. 430-432 (2003).

* cited by examiner

*Primary Examiner* — Jerry Lin

(57) ABSTRACT

The present invention consists of a time-temperature indicator device that has at least one parameter set to warn when a therapeutic protein drug has had a thermal history associated with increased risk of unwanted immunological activity. The indicator device is designed to remain with the drug as the drug travels throughout different links of the cold chain. In a preferred embodiment, the indicator device remains associated with the therapeutic protein from the time of manufacture up until the final few minutes before the drug is used. In alternate forms of the invention, additional parameters, including motion, light, color and turbidity may also be monitored. Novel methods for determining therapeutic protein time-temperature immunological risk parameters, and programming or adjusting the indicator device, are also disclosed.

17 Claims, 10 Drawing Sheets

METHOD AND DEVICE TO DETECT THERAPEUTIC PROTEIN IMMUNOGENICITY

This application is a continuation in part of, and claims the priority benefit of, U.S. patent application Ser. No. 10/747,926 "Method and device to detect therapeutic protein immunogenicity." filed Dec. 29, 2003 now abandoned. Application Ser. No. 10/747,926 in turn claimed the priority benefit of provisional patent application 60/465,434, "Electronic time-temperature indicator", filed Apr. 25, 2003, as well as provisional patent 60/496,358 "Method and device to reduce therapeutic protein immunogenicity", filed Aug. 18, 2003, and patent Ser. No. 10/634,297 "Electronic time-temperature indicator", filed Aug. 5, 2003 (now U.S. Pat. No. 6,950,028). The present application is also a continuation in part of, and claims the priority benefit of, U.S. application Ser. No. 11/515,310 "Material lifetime data abstraction device and method", filed Sep. 1, 2006 now U.S. Pat. No. 7,564,364. Application Ser. No. 11/515,310 is a continuation in part of, and claims the priority benefit of, U.S. patent Ser. No. 10/824,709 "Electronic time-temperature indicator and logger", filed Apr. 14, 2004, (now U.S. Pat. No. 7,102,526). The Ser. No. 10/824,709 application was a continuation in part of application Ser. No. 10/634,297 "Electronic time-temperature indicator, filed Aug. 5, 2003, since issued as U.S. Pat. No. 6,950,028. The Ser. No. 10/634,297 application in turn claimed the priority benefit of provisional patent application 60/465,434, "Electronic time-temperature indicator", filed Apr. 25, 2003; and provisional patent applications 60/502,834 and 60/506,814, "Electronic time-temperature monitor and logger", filed Sep. 12, 2003 and Sep. 26, 2003.

BACKGROUND OF THE INVENTION

1. Field of the Invention

This patent application covers methods and devices by which unwanted immune responses against therapeutic proteins may be detected and prevented.

2. Description of the Related Art

Recent advances in genetic engineering and biotechnology have enabled the creation of a number of advanced biotherapeutic drugs, which are usually therapeutic proteins produced by recombinant DNA techniques. These drugs, such as recombinant insulin, interferon, erythropoietin, growth hormone, and the like, have revolutionized modern medicine.

One thing that most modern biotherapeutic drugs have in common is that they often are recombinant DNA cloned versions of natural proteins and protein hormones, or are modified versions of natural proteins. As such, most biotherapeutics have a much higher molecular weight than traditional pharmaceuticals. Additionally, most biotherapeutics tend to be somewhat delicate. Whereas most traditional pharmaceuticals are small molecules, typically robust and resistant to deterioration caused by temperature storage effects, this is not the case for therapeutic proteins. Many biotherapeutic drugs are dependent upon the correct conformation of their protein components. As a result, biotherapeutics are quite temperature sensitive. Many cannot tolerate freezing, because freezing tends to denature proteins and cause the formation of protein aggregates. Many also cannot tolerate storage temperatures much above refrigerator temperatures, since higher temperatures can also promote protein denaturation and formation of protein aggregates. As a result, most modern biotherapeutics must be carefully temperature controlled from the time of manufacture, to the time they are used by the ultimate end user.

The immune system is a complex network of immune system cells, antibodies, cytokines, and other regulatory components designed to detect and destroy foreign (non-self) molecules, while at the same time not attacking native (self) molecules. Thus molecules that naturally occur in the body exhibit immune tolerance. The biological reason for this should be clear, since it is obviously undesirable for the body to attack its own naturally occurring components. Biotherapeutics, by virtue of the fact that they are synthetic analogs of naturally occurring proteins, also are often covered by this same immune tolerance system. Thus medical practice typically assumes that a biotherapeutic that is an analog of a naturally occurring molecule should generally be capable of administration without undue concern for provoking an immune reaction. However as the structure of a biotherapeutic molecule diverges from a native molecule, the possibility of it triggering a "foreign molecule-attack" immune response increases. In particular, the immune system often recognizes protein aggregates as "non-self", and mounts an immune response against them. Such targets of immune system attack are commonly referred to as "antigens".

Although modern biotherapeutics have saved countless thousands of lives, and improved the quality of life for countless others, as their use has increased, it has become apparent that the drugs occasionally exhibit unwanted side effects. One of the most distressing side effects is the occasional development of an unwanted immune reaction against the biotherapeutic. This effect is discussed in Rosenberg, *Immunogenicity of Biological Therapeutics, A Hierarchy of Concerns*, Dev. Biol. Basel, Karger 2003, Vol 112, pp 15-21. These unwanted reactions are sometimes referred to as HADA (human anti-drug antibody) effects.

As discussed in Chamberlain, *"Immunogenicity of Therapeutic Proteins"*, The Regulatory Review 5:5, August 2002, pp 4-9, such unwanted immune responses can range from mild responses, to very severe responses. In the mild case, which often occurs for diabetics exposed to partially degraded insulin delivered by insulin pumps, antibodies against the biotherapeutic partially neutralize the biotherapeutic, requiring the dose of the biotherapeutic to be increased in order to achieve the same therapeutic effect. Thus in this insulin pump example, affected diabetics require increasingly larger doses of recombinant human insulin in order to achieve good blood glucose control. In other cases, such as has been seen with recombinant erythropoietin (which is a recombinant protein analog to a naturally produced red cell production stimulating hormone), more serious effects can occur. Erythropoietin is often used to stimulate red blood cell production in anemic patients. However antibodies induced by the recombinant erythropoietin biotherapeutic can bind to naturally produced erythropoietin. This can lead to the complete cessation of all subsequent red cell production. This later condition, called "red cell aplasia" can be fatal unless treated by blood transfusion and/or immunosuppressive drugs.

Although vibration, shaking, or light exposure can facilitate the degradation of therapeutic proteins, these effects are usually minor, relative to temperature effects.

It is generally recognized that upon storage, therapeutic proteins degrade by a variety of time-temperature dependent processes, including denaturation, aggregation, oxidation, deamidation, disulfide exchange, and proteolysis. Studies have shown that this time and temperature dependent storage degradation can create immunogenic byproducts, such as protein aggregates, and further have shown that the formation of these immunogenic byproducts is accelerated at higher storage temperatures (Hochuli, *"Interferon Immunogenicity:*

*Technical Evaluation of Interferon α2α*", J. Interferon and Cytokine Res. 17 supplement 1: S15-S21, 1997).

Although storing therapeutic proteins at a lower temperature can minimize a number of these processes, other temperature effects often impose a practical lower temperature storage limit. Upon freezing, for example, many proteins undergo conformational changes that can also lead to denaturation, and aggregation. Thus in practice, therapeutic proteins are optimally stored in a rather narrow temperature range, typically 2-8° C.

Curiously, although it is well known that therapeutic proteins are very sensitive to the effects of time and temperature on storage, in general, the biotechnology and pharmaceutical industry has exhibited a profound lack of curiosity as to the effect on biological therapeutics of storage at temperatures other than refrigerated temperature (2-8° C.), room temperature (generally 23-25° C.), or mild elevated temperature (30° C.). There are very few published studies discussing stability outside of these few specified temperature conditions. This lack of curiosity may be due, in part, to the pharmaceutical industry's tradition of working with small molecule drugs, which are typically less temperature sensitive, less immunogenic, and which usually exhibit tolerance to a broad range of storage conditions. In general, the unstated assumption for biotherapeutics has been that it is adequate to simply characterize a therapeutic protein's temperature stability at a few points, and assume that the therapeutic protein will never encounter any other type of temperature conditions after initial shipment.

At present, when pharmaceutical products are shipped, it is standard practice to include temperature monitors as shipping indicators. These monitors, such as the HOBO time-temperature data logger produced by Onset Computer Corporation, Pocasset, Mass.; the Monitor In-transit temperature recorder; the TagAlert® and TempTales® monitors, produced by Sensitech Corporation, Beverly Mass.; and others; inform users if the drug has been exposed to temperature extremes during shipment. However after shipment, such monitors are typically removed.

Similarly, it is common practice to store drugs in refrigerators, which when run in a properly managed health care practitioner setting, will also be monitored and controlled. Normally, however, drugs are stored in more than one refrigerator during their storage lifetime, and this is where problems can occur.

Note that at present, the cold chain between the manufacturer and the ultimate end user has many interface boundaries. At these boundaries, time-temperature monitoring by one system ends, and monitoring by a different system begins. The time and temperature conditions in the boundary between these different systems is usually not monitored or tracked.

Clearly, it is unrealistic to assume that in all steps and interface regions of the cold chain between the pharmaceutical manufacturer and the ultimate use by the health care practitioner or patient, all protein therapeutics will always be carefully temperature controlled. Other areas of medicine do not make such optimistic assumptions. In medical diagnostics, for example, manufacturers and regulators assume that recommended storage and handling conditions may, in fact, be violated. As a result, diagnostics manufacturers and regulators often require that medical diagnostic products incorporate one or more controls or detection methodologies to detect if the diagnostic's recommended storage and handling conditions have been violated. Such approaches are taught by U.S. Pat. No. 6,629,057, and other technology. In this respect, the disparity of practice between the medical diagnostics industry, and the biotherapeutic industry, is quite large.

One explanation for the difference in practice between the medical diagnostics industry and the biotherapeutic industry is ease of quantitation. Medical diagnostics are designed to rapidly convey large quantities of precise numeric information as to their operating condition. Thus problems can be quickly and easily detected. By contrast, biotherapeutics are more difficult to assay, and immunogenicity assays are particularly difficult. However given the now large number of cases in which immunological complications of protein biotherapeutics have been reported, it is clear that these issues need to be addressed.

Consider, for example, the consequences of improper storage conditions on three different products: the first is a food product, the second is a medical diagnostic, and the third is a biotherapeutic protein. In the first case, customers will quickly detect food degradation, either through "off" taste, or possibly food sickness, and the improper storage will be quickly discovered and corrected. In the second case of a medical diagnostic product, the improper storage will also be quickly detected when lab operators run controls, and obtain aberrant answers. Here too, improper storage will be quickly discovered and corrected. However in the third case of a therapeutic protein, the results may be quite different. On a somewhat random basis that may correlate with shipment or storage history, but which will usually not correlate with specific manufacturing lot numbers, certain patients may develop inexplicable immune reactions against the therapeutic protein. This will typically occur many months after the fact. Given the large time lag, difficulty of detection, and the random nature of improper storage conditions, the cause may never be discovered. Yet at the same time, the consequences may be severe. A therapeutic protein pharmaceutical product, or indeed an entire class of therapeutic protein pharmaceuticals, may be subject to regulatory delay or outright recall, affecting the medical status and prognosis of thousands of patients worldwide.

Whether a potentially antigenic therapeutic protein proceeds to produce a clinically unacceptable immune response in a patient depends upon a number of additional factors. Patients differ in their genetic makeup, with some patients tending to be antigen "responders", and some tending to be antigen "non responders". Additionally, the route of administration of the antigen may play a role. Mounting an immune response generally takes time. Therapeutic proteins administered in a localized depot, such as by subcutaneous injection, which slowly produces a higher localized level of antigen, may produce a higher immune response than therapeutic proteins administered by an intravenous route. Although differences in patient genetic makeup and route of administration will clearly have an impact on the development of an unacceptable immune response, clearly a key strategy is to simply avoid using potentially antigenic therapeutics in the first place.

Currently, the biotechnology industry expends a great amount of effort in optimizing the chemistry of biotherapeutics, with the goal of minimizing immunogenicity. These efforts include humanizing monoclonal antibodies, modifying the structure of the biotherapeutic proteins, and optimizing the pH, buffer, and carrier molecules that help preserve the original biotherapeutic shape and structure. However in contrast to this extensive amount of effort to optimize biotherapeutic chemistry, a relatively small amount of effort is devoted to monitoring the storage conditions that can cause chemical modifications and antigen formation upon prolonged biotherapeutic storage.

In medical diagnostics, and in many other areas, causes of failure are often analyzed by FMEA (Failure Modes Effects Analysis). This type of analysis allows failure modes to be numerically ranked in order of importance, based upon the severity of the failure, the frequency of occurrence of the failure, and the ability to detect the failure in a timely manner. More severe failures are given a high numeric first coefficient, more frequent failures are given a high numeric second coefficient, and hard to detect failures are given a high numeric third coefficient. Easy to detect failures are generally given a low numeric rating, since failures that can be easily detected can then usually be counteracted quickly. The three coefficients are then multiplied, and the magnitude of the resulting FMEA rating is used as a guide to determine the order and priority in which failure modes should be addressed. Higher FMEA ratings are more urgent, and are generally given a higher priority for subsequent corrective action.

FMEA analysis can be used to examine the three examples of improper storage conditions discussed previously. The first example, improper food storage, although important, would generally be given a medium FMEA priority because the failure is usually simply customer dissatisfaction or gastric distress, and the ability to detect the failure is high. Improper medical diagnostics storage might be given a somewhat higher priority, due to the fact that the impact severity, possible misdiagnosis of a patient, is often quite high. However since control tests are mandated, and frequently performed, the detectability is also high, and the good detectability FMEA coefficient reduces the overall FMEA ranking. By contrast, improper shipment or storage of a protein therapeutic will typically generate a very high FMEA score. The failure mode, possible patient adverse reaction to the drug, possible death, and possible recall of an otherwise promising therapeutic, is extremely severe. At the same time, using current practice, a number of storage condition failures are often difficult or impossible to detect, due to lack of appropriate devices to continually monitor the material at all steps of the cold chain. This combination of high impact and low detectability is quite undesirable. As the frequency of such events increases, the subsequent FMEA ranking may get very high.

At present, pharmaceutical manufacturers are primarily focused on reducing the severity and frequency portion of the FMEA analysis by employing chemical strategies intended to reduce the potential antigenicity of the therapeutic proteins. Although this effort is justified and commendable, FMEA analysis shows that there is another way to reduce risk. This is by improving the detectability of the failure. Health care practitioners or patients who are aware that a particular vial of therapeutic protein has a potential immunogenicity issue due to improper storage or handling can simply avoid using that particular vial. This can be done by incorporating monitoring means with the vial that stay with the vial throughout the cold chain, and that can warn the user about potential immunogenicity issues. Although traditionally, limitations in sensor technology have made such efforts technically or economically infeasible, the rapid advance in modern low cost electronics, instrumentation and detection chemistry, as well as the comparatively high economic value of each vial of therapeutic protein, now make such efforts feasible.

SUMMARY OF THE INVENTION

The present invention consists of a time-temperature indicator device that has at least one parameter set to warn when a therapeutic protein drug has had a thermal history associated with increased risk of unwanted immunological activity. The indicator device is designed to remain with the drug as the drug travels throughout different links of the cold chain. In a preferred embodiment, the indicator device remains associated with the therapeutic protein from the time of manufacture up until the final few minutes before the drug is used. In alternate forms of the invention, additional parameters, including motion, light, and turbidity may also be monitored. Novel methods for determining therapeutic protein time-temperature immunological risk parameters, and programming or adjusting the indicator device, are also disclosed.

At least one of the parameters of the time-temperature indicator devices of the present invention is determined by tests for immunological stability, which is distinct from functional stability. The final stability of the therapeutic protein is determined based on a function that incorporates both the time and temperature profile required to maintain functional activity, and the time and temperature profile necessary to avoid the production of therapeutic protein degradation products that are typically associated with risk of unwanted immunological activity.

Since the immune system is extremely sensitive, only a small amount of degradation, on the order of a few percent or less of the total material, may trigger an unwanted immune response. Thus often, such degraded material, although now immunologically unacceptable, may otherwise still perform adequately in all other therapeutic areas. For example, a therapeutic protein may lose from <1% to 10% of its protein to a degraded and potentially antigenic form, yet not show any significant change in functional activity, since 90 to 99% of the material would still be unaffected. Thus typically the immunological stability of a therapeutic protein is affected before the functional stability of the protein is affected. That is, a protein tested and released to strict immunological stability standards will typically have a restricted time and temperature stability profile, relative to proteins tested and classified only by standard (and non-immunological) functional stability criteria.

Such indicators could be particularly useful for biogenerics. Biogenerics are therapeutic proteins that have gone "off patent", and are now produced by alternate manufacturers as generic drugs. Such biogenerics are often produced by methods that are slightly different from the original proprietary form of the therapeutic protein. Given the complexity of large molecular weight proteins, there is a potential risk that the new manufacturing processes will produce products may, upon temperature stress, degrade into material that creates an immunological risk. Such risks can be mitigated by carefully characterizing the environmental conditions likely to produce antigenic protein degradation products, and programming this data into indicator devices that can remain associated with the biotherapeutic throughout its product life.

DETAILED DESCRIPTION OF THE INVENTION

Figure 1:
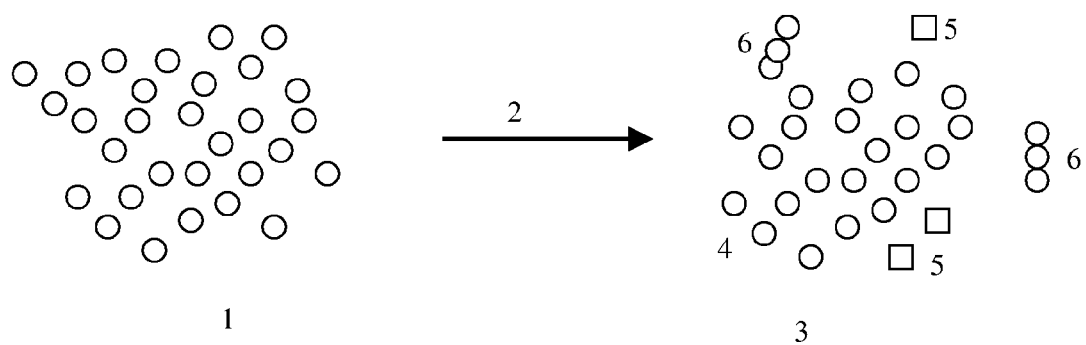
FIG. 1 shows a population of therapeutic proteins before and after thermal stress.

The disclosures of application Ser. Nos. 10/747,926; 10/634,297; 11/515,310; and 10/824,709 are incorporated herein by reference.

Although the concept of monitoring storage containers of therapeutic agents is not new, in the past, such monitoring has been focused entirely on detecting loss of therapeutic activity, rather than in detecting formation of unwanted immunogenic activity.

Prior examples of monitored therapeutic agents include HeatMarker® Time-Temperature indicator (LifeLines Technology, Morris Planes, N.J.) labeled vaccine vials. These are useful for distributing vaccines in third world countries, where vaccines may become inactive (loose their immunogenic potential) due to exposure to high temperatures for too long a time. Here, the indicator device is a temperature sensitive label stuck to the outside of a vaccine vial. The label changes color in response to exposure to high temperatures for too long a time, and thus warns the user if the vaccine has degraded (lost immunological activity).

These previous combination therapeutic agent containers-environmental detector systems differ from the present invention in that, for the case of vaccines, antigenic activity is an essential component of the therapeutic. Here the detectors are designed to detect temperature-induced loss of antigenic activity. By contrast, the present invention is designed for therapeutic agents that are not normally antigenic, and indeed where antigenic activity is unwanted. An additional difference is that the prior art indicators, being chemically mediated, typically were insensitive to freezing conditions, where proteins frequently denature and start to exhibit antigenic activity.

The present invention has two aspects. The first aspect of the invention is based upon the concept of using "immunological stability" as one of the primary criteria for determining the shelf life and storage conditions of therapeutic proteins, and using this data as a key input into the final assessment of the therapeutic's final "acceptable stability" profile. Here, the utility of using immunological stability for shelf life dating is proposed, along with various methods to determine immunological stability shelf life and storage conditions.

In the second aspect of the invention, indicator devices are disclosed that continually monitor a therapeutic protein's storage conditions, and warn users when the immunological stability profile of the therapeutic has been exceeded, and can also warn when other time-temperature storage criteria have been exceeded.

As previously discussed, as a therapeutic protein degrades, often antigenic activity may develop before the extent of degradation is large enough to produce a significant change in the therapeutic efficacy of the protein. This is because, for example, a protein changing from a 100% monomeric state to a 95% monomeric, 5% aggregated state will typically suffer, at most, only a 5% loss in potency, which is generally too small to be observable. By contrast, the concentration of the potentially antigenic aggregates will have changed from 0% to 5% of the total amount of therapeutic protein, which is essentially an infinite increase. As a result, antigenic degradation limits will often impose more stringent time and temperature limits on a therapeutic protein's lifetime then will potency loss limits.

To avoid unwanted side effects due to antigenic activity, more stringent "antigenic generation" criteria should be used to determine the storage stability of biological therapeutics.

FIG. 1 shows a diagram of some of the fundamental biochemistry and immunology behind the present invention. That is the difference between a therapeutic protein's functional stability, and a therapeutic protein's immunological stability.

FIG. 1 shows some of the mechanisms by which a therapeutic protein can deteriorate as a result of suboptimal storage conditions (excess temperature for too long a time, freezing, etc.). When freshly manufactured, therapeutic proteins typically exist as a homogenous population of non-aggregated, active, molecules (1). Upon suboptimal temperature storage or other adverse conditions (2), this homogeneous population of molecules can undergo a number of different degradation reactions. In the degraded population (3), many of the therapeutic protein molecules retain their original conformation, and activity. Thus from a functional standpoint, this degraded population may contain enough functional therapeutic proteins (4) so as to retain normal functional activity. From a functional stability standpoint, population (3) is still acceptable.

However from an immunological stability standpoint, the situation may be different. FIG. 1 shows two possible degradation modes. One harmless degradation mode, shown in (5) may produce degraded proteins that may or may not have degraded functional activity, but are not inherently more antigenic, or prone to stimulate unwanted immunological reactions.

FIG. 1 also shows a second harmful degradation reaction that produces immunogenic protein aggregates (6). These protein aggregates may, or may not, have degraded functional activity, and may be undetectable in a functional assay. However as the concentration of protein aggregates increases (6), the chances for an undesired immunological reaction also increase.

Figure 2:
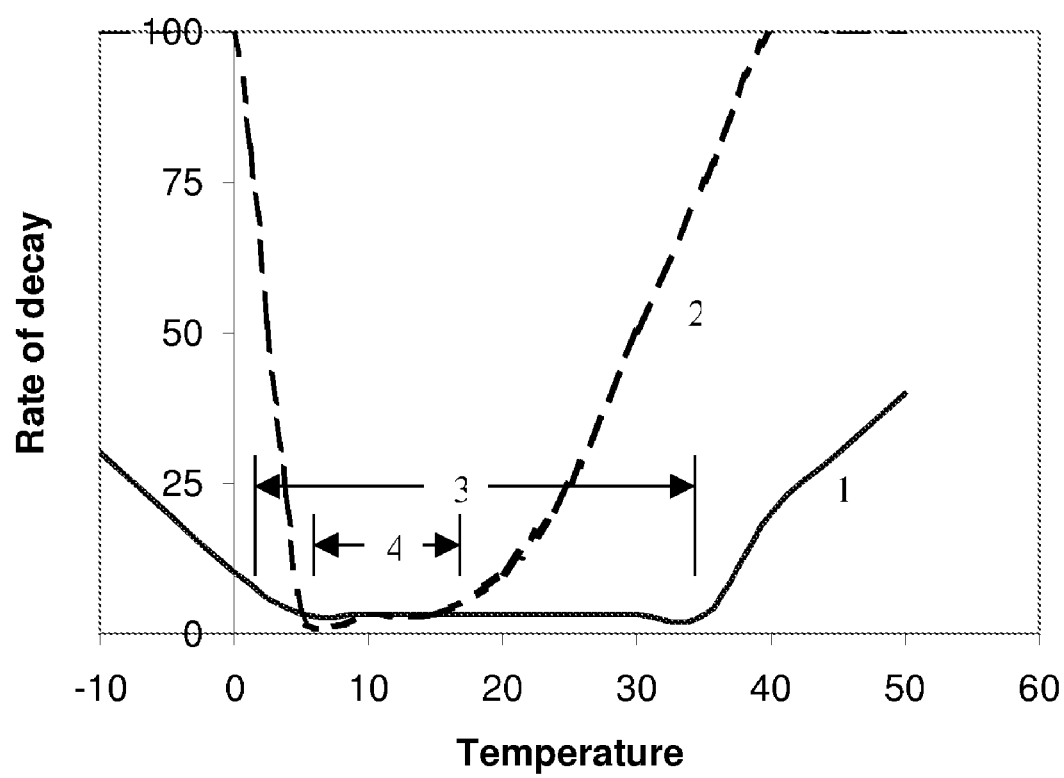
FIG. 2 shows a hypothetical stability profile for a therapeutic protein.

FIG. 2 shows a graph showing the rate of deterioration of a hypothetical therapeutic protein at various temperatures. FIG. 2 (1) (line 1) shows the rate of deterioration of the functional activity of the protein. Typically this deterioration is due to the sum of all degradation processes that operate upon the protein, and the amount of deterioration only becomes large when the sum of all degradation processes significantly reduces the total concentration of active therapeutic protein.

FIG. 2 (2) (line 2) shows the rate of formation of immunologically active deteriorated protein components. Typically, only a very small amount of immunologically active deteriorated protein needs to be produced to create immunologic (HADA) stability issues. Additionally, only some of the deteriorated protein products, such as formation of aggregates, may be responsible for unwanted immunological activity. As a result, line 2 often, but not always, may show greater temperature sensitivity than line 1. In this diagram, the effective optimal stability temperature from the standpoint of functionality is shown as (3), and the effective optimal stability temperature from the standpoint of immunological activity is shown as (4).

In the case where the immunological activity time-temperature range is broader (more robust) than the functional activity time-temperature range, no adjustment in therapeutic protein stability time temperature lifetime criteria is needed because the functional time-temperature stability profile are conservative, and protect patients from unwanted immunological activity. However in the more frequent case where the immunological activity time-temperature range is narrower (less robust) than the functional activity time temperature range (illustrated in FIG. 1), then to avoid potential unwanted immunological side effects, the time-temperature stability profile of the therapeutic protein should be revised.

Methods to Monitor the Immunological Stability of Therapeutic Proteins

In certain cases, immunological stability considerations may cause the time-temperature storage characteristics of a therapeutic protein to be substantially derated, relative to its nominal functional stability profile. Although occasionally, a simple labeling change, in which a therapeutic is simply given a more conservative set of storage temperatures and storage lifetime, will be sufficient way to address these issues, often this will not be enough. In order to provide a robust solution that is capable of coping with the inevitable disruptions in the cold chain that will occur with large-scale commercial distribution, (discussed in the earlier FMEA analysis) it will often be desirable to incorporate active time-temperature monitoring means into the therapeutic protein's storage container.

As a less favored embodiment of the present invention, chemistry based integrating time-temperature indicators may be used. For example, the LifeLines HeatMarker® (Baughman et. al. U.S. Pat. No. 4,389,217, Prusik et. al. U.S. Pat. No. 6,544,925) or 3M MonitorMark® (Arens et. al. U.S. Pat. No. 5,667,303) colorimetric time-temperature monitors may be used. However since therapeutic proteins are typically subject to deterioration at both low and high thermal conditions, standard chemical time-temperature indicators, which typically only trigger on higher temperatures, and may not precisely model the exact characteristics of the therapeutic drug, may not be adequate for all situations.

A more favored embodiment of the present invention is based upon the improved electronic time temperature indicators disclosed in copending U.S. patent application Ser. No. 10/634,297, "Electronic time-temperature indicator", filed Aug. 5, 2003, and incorporated herein by reference. These electronic time-temperature indicators can be made to be highly accurate, and customized to address nearly any conceivable set of time-temperature algorithmic criteria. Other electronic time-temperature monitors, such as those disclosed in Berrian et. al., (U.S. Pat. No. 5,313,848; and subsequently reexamined and reissued as Re. 36,200), may also be used, whenever the immunological and chemical parameters of the biotherapeutic in question allows the less flexible time-temperature performance of this earlier technology to be used.

Although non-indicating time-temperature indicators, such as radio frequency identification (RFID) tag time-temperature indicators, such as the Bioett RFID tag (Sjoholm et. al. WIPO application WO0125472A1), or electronically communicating temperature loggers, such as the Dallas Semiconductor iButton (Curry et. al. U.S. Pat. No. 6,217,213) may also be used, these are generally less preferred, because these systems lack visual displays capable of giving immediate feedback to healthcare practitioners and/or patients.

Figure 3:
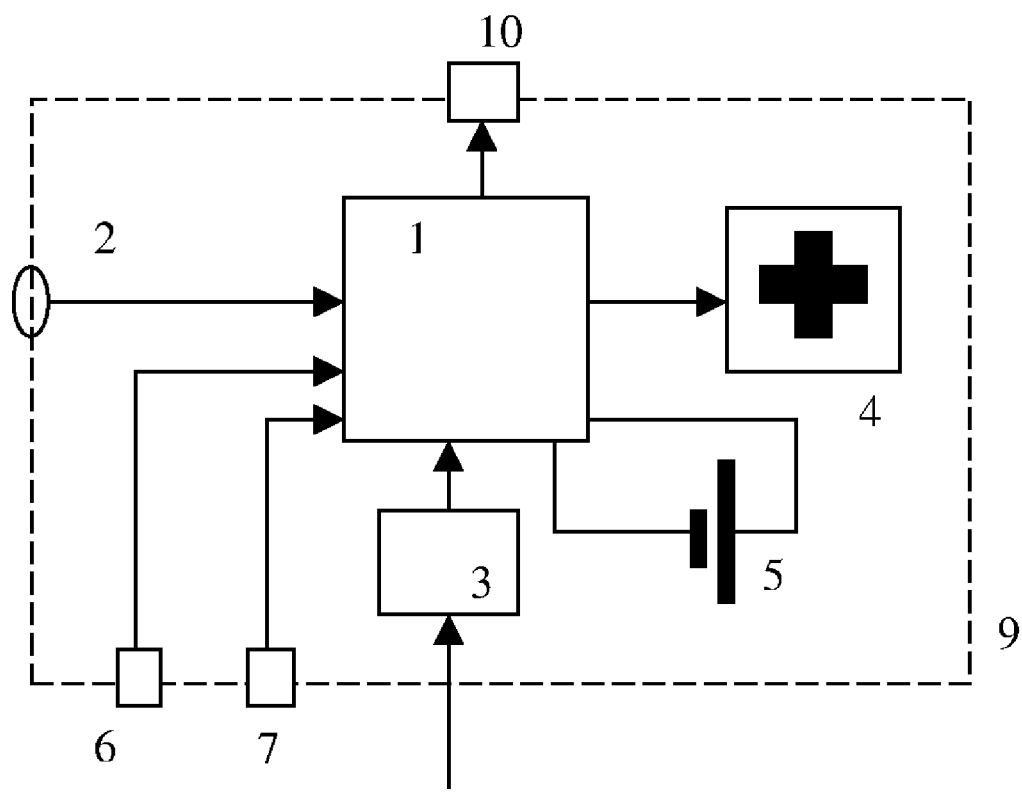
FIG. 3 shows a programmable time-temperature indicator.

FIG. 3 shows an electrical schematic of a preferred time-temperature indicator, constructed according to the teaching of commonly owned U.S. Pat. Nos. 6,950,028 and 7,102,526 that is well suited for use in the present invention. This has a microprocessor or microcontroller (1) receiving thermal input data from a temperature sensor, such as a thermocouple or thermistor (2). The microprocessor (1) further receives algorithms from stability memory (3) containing instructions for converting the thermal data into numeric data proportional to the stability impact of the measured temperature upon the monitored material. Microprocessor (1) will typically contain an onboard timer, as well as other general programming information in its own onboard memory.

Microprocessor (1) will have at least one output means. Usually this output means will be a visual output means, such as a liquid crystal display ("LCD") (4). Other output means, such as LEDs, sonic alarms, vibration, radio frequency signals, electrical signals, and infrared signals may also be used. This output means, here exemplified by a liquid crystal display, will at a minimum be able to convey to the user the information that the stability characteristics of the unit have been determined to be acceptable (here designated by a "+" symbol), or non-acceptable (here designated by a "−" symbol).

Although other power sources are possible, microprocessor (1), and other power consuming circuitry in the unit, will typically be powered by battery (5). An example of such a battery is a 1.5 Volt or 3 Volt coin cell.

The microprocessor may optionally have manufacturer input means, such as a reset button (6) that zeros and reinitializes the unit. The microprocessor may also optionally have a second user input means, such as a test button (7), that may instruct the unit to transmit supplemental temperature statistical data.

In order to make the time-temperature unit as versatile as possible, the processor memory containing the material stability data (3) may be designed to be a rewriteable memory, such as an electrically erasable programmed read only memory (EEPROM), or flash memory. This EEPROM or flash memory may be reprogrammed by signals from a programming device external to the unit (8). Alternatively, the stability data may be on a replaceable chip (such as a memory card chip), or other memory storage device, which is plugged into the unit, or be an integral part of the microprocessor's own nonvolatile memory.

It is generally convenient to place all the circuitry, including the battery, processor, thermistor (temperature sensor), buttons, and display into a unitized case (9), so as to present a single device or unit to the user. This device may optionally have attachment means, such as adhesive, Velcro, hooks, snaps, etc., to enable the device to be attached to the vial or container holding the therapeutic proteins. If data output is desired, optional infrared, electrical, or radio frequency port (10) may be used to output relevant temperature statistics and other verification data upon pressing of the test button (7).

Typically, to allow more precise monitoring of the therapeutic protein's temperature, the thermocouple or temperature sensor (2) may be embedded into the case wall, or mounted outside of the case. These later configurations may be preferred for situations where the monitor will be stuck directly onto the material to be monitored. In a fourth configuration, temperature sensor (2) may be mounted in the hole or junction between the case and the inside of the therapeutic protein package, and be directly exposed to the interior of the package, gaining some physical protection while minimizing thermal interference from the case wall itself.

As previously discussed, to allow this device to be rapidly customized for a particular therapeutic protein, it is advantageous that the stability lookup table or conversion function data be stored in a non-volatile read-write storage medium, such as Electrically Erasable Programmable Memory (EEPROM), flash memory, or equivalent. However if this convenience is not desired, and cost minimization is priority, a non-reusable memory, such as a programmed read only memory (PROM), or read only memory (ROM) may also be used.

In some embodiments, the stability data stored in (3) may be in the form of a lookup table. In alternate embodiments, the data may be stored in the form of a mathematical function that automatically generates the equivalent information. Microprocessors suitable for the present invention are typically ultra low power microprocessors, with a corresponding long battery life. These microprocessors may additionally incorporate a number of onboard functions such as timers, liquid crystal display drivers, analog to digital converters, and circuitry to drive temperature sensors. The MSP430 family of microprocessors, such as the MSP430F412, produced by Texas Instruments, Inc., exemplifies one such microprocessor type. This processor family includes members with onboard reprogrammable flash memory, as well as analog to digital ("A/D") converters, timers, LCD drivers, reference current sources to power sensors, and other functions. Here, the stability data may be directly downloaded into the flash memory on the same chip that holds the other processor components.

Other types of time temperature monitor, or other environmental monitor, may also be used. As one example, if the therapeutic protein is sensitive to vibration or motion, the monitor may also have motion-sensing means. If the therapeutic protein is sensitive to light, the monitor may also have light sensing means. If the therapeutic protein forms turbidity in response to environmentally induced damage, light scattering sensing means may also be used. Typically the monitor will have at least an ability to monitor both time and a function of temperature, so as to adequately warn if the effects of temperature over time on the therapeutic protein are leading to the formation of undesirable immunological byproducts.

Methods to Determine Onset of Immunogenicity:

Although the simplest and most direct method to determine the time-temperature degradation threshold where therapeutic proteins become antigenic is by experimental injection and immune response detection, such methods are usually infeasible.

In the direct approach, samples of the therapeutic protein are stressed to a varying extent, and used to immunize experimental subjects. Although humans are the most realistic subjects, this is legally and ethically impermissible, and thus experimental alternatives must rely upon model animals such as mice, which many not accurately reflect the immune response of a human population.

Thus due to the complexity of the immune response, and the infeasibility of working with the large numbers of human subjects required to get a definitive assessment, typically more indirect immunological risk assessment methods must be used.

At present, immunogenicity risk is primarily assessed by indirect methods, which monitor the physical degradation or change in the protein, and attempt to assess when such changes are likely to trigger an immunological reaction.

In general, aggregated proteins tend to be more immunogenic than non-aggregated proteins, and the progressive development of protein aggregates is a good marker for potential immunogenic activity. Thus one of the simplest immunogenic reactivity methods is to monitor the time-temperature storage conditions that promote the formation of larger molecular weight protein aggregates.

Methods to monitor protein aggregate formation include light scattering, size exclusion chromatography, centrifugation, mass spectroscopy, and other methods.

In addition to aggregation assays, other protein degradation methods are discussed in Hochuli (previously cited, and incorporated herein by reference). Additionally, other methods are also possible, which are discussed in the following section.

Example 1

Protein Surface Mapping

Environmentally induced degradation of therapeutic proteins will frequently result in a conformational change in the protein. This conformational change becomes particularly problematic when the change in the protein conformation is large enough so as to substantially alter the immunological profile of the protein.

These changes can be assessed by using enzymatic-labeling techniques, which label exposed residues on the surface of biological proteins.

Here the therapeutic protein of interest is labeled or modified by a variety of enzymatic methods. These methods may include protease digestion, posttranslational modification, labeling with a tag that produces a detectable signal, or any method that requires steric access to the protein surface in order to modify the protein structure. The protein may then be fragmented into different peptides by various means (enzymatic digestion, chemical cleavage, etc.), and the amount of label on each fragment, or the presence or absence of digestion products, quantitated by various methods, including peptide mapping, capillary electrophoresis, mass spectrometry, etc.

These labeling experiments are done using both fresh protein, and degraded protein. Those peptide fragments that are associated with degraded proteins may be used as markers to monitor the formation of potentially immunogenic degradation epitopes.

Here, it will be useful to first calibrate these methods on therapeutic proteins with previously characterized immunogenic capability. By compiling a large library of comparative data, an expert system (computerized or otherwise) may be developed that with an ability to correlate changes in therapeutic conformation with development of potential immunogenic activity.

Example 2

Comprehensive Mapping of all Potentially Immunogenic Therapeutic Protein Epitopes This technique uses phage display technology, which is reviewed by Petrenko, J *Microbiol Methods*. 2003 May; 53(2):253-62; Coomber, *Methods Mol Biol*. 2002; 178:133-45, and others. Alternatively, ribosome display technology, reviewed by Ling, *Comb Chem High Throughput Screen*. 2003 August; 6(5):421-32 or more traditional lymphocyte monoclonal antibody technology may also be used.

Although this comprehensive mapping technique has not been described in previous literature, and thus appears to be a novel aspect of the present invention, it has the potential for creating direct links between protein degradation, the immune response capability of large populations of human subjects, and the development of unwanted immunogenicity.

Here, a phage display or ribosome display library consisting of many different types of antibody genes, or alternatively immune response genes (MHC antigens, Ia antigens' etc.), representative of the various genes distribution in the drug's target population, may be used to construct a "stability epitope map" of the therapeutic protein's temperature or environmentally sensitive regions.

To do this, the phage display or ribosome display library is used to create several libraries of different monoclonal antibodies (or other immune response receptor molecule) with activity against essentially all potential epitopes on the therapeutic protein. These libraries consist of panels of different monoclonal antibodies that bind to different specific regions of interest (epitopes) on the therapeutic protein under investigation. One library might represent the target population's (e.g. the human population that are potential users of the drug) potential capability to mount an immune response against various epitopes on the environmentally stressed therapeutic protein. A second library would represent the target population's potential capability to mount an immune response against the fresh (non environmentally stressed) therapeutic protein. Those monoclonal antibodies (or other immune response receptor molecule), that detect only the new epitopes produced upon thermal environmental stress of the therapeutic protein (anti-degradation specific epitopes) can then be used to form the basis of a "differential immunogenicity risk" assay.

This panel of degradation epitope monoclonal antibodies can then be used to map out the precise details of the therapeutic protein's environmental sensitivity profile. For example, samples of the therapeutic protein may be stressed over comprehensive range of times and temperatures spanning all possible field thermal environments (for example 2° C., 4° C., 6° C. ... 38° C., 40° C. ... 48° C., 50° C.) and over all possible time values up until product expiration (e.g. 1 month, 2 months ... 12 months ... 18 months). This two dimensional array of stressed therapeutic proteins can then be analyzed using the panel of degradation epitope monoclonal antibodies, and the response curve of time and temperature versus degradation epitope production ascertained.

Next, using historical data based upon comparative studies of therapeutic proteins, which are known to exhibit an acceptable level of immunogenic activity in the general population, a maximum acceptable level of reactivity in the degradation epitope assay is determined. Using this maximum acceptable level, the curve representing the maximum time at each temperature level before the therapeutic protein if interest exceeds the maximum level of reactivity is determined. This is used to produce a time-temperature curve representing the amount of time at any given temperature that the therapeutic protein can exhibit before the risk of unwanted antigenic activity becomes too great.

This data may then be used as input into various types of time-temperature indicator, which then may be affixed to the storage container of the therapeutic protein of interest, forming a unitized device that is continually available to health care workers.

In a modification of this technique, phage display technology may also be used to create a differential epitope map between a natural protein, and a manufactured therapeutic protein, and can be also used to optimize the biochemistry of the manufactured therapeutic protein for maximum immunological stability.

Example 3

Monitoring the formation of protein aggregates. Methods to characterize protein aggregates are well known in the field. One good example is disclosed in the work of DePaolis et. al., "Characterization of erythropoietin dimerization", J Pharm Sci. 1995 November; 84(11):1280-4. Protein aggregates typically exhibit a large change in molecular weight, which can be monitored by essentially any method sensitive to changes in molecular weight.

Once the relevant time-temperature storage conditions associated with immunogenic risk have been identified, the next step in the present invention is to devise or program suitable time-temperature indicators that can warn users when an unacceptable thermal exposure has occurred. Example 4, shown below, shows how this is done, using the "poster child" of unwanted immunogenic reactions, the recombinant drug "Eprex™", as an example.

Example 4

Use of an Electronic Time-Temperature Indicator to Monitor the Immunological Stability of Various Erythropoietin Drugs As previously discussed, certain temperature sensitive forms of Erythropoietin (EPO) have shown a strong correlation with subsequent generation of autoimmune responses against natural erythropoietin. In particular, the human serum albumin (HSA) free formulation of Eprex has a history of being particularly problematic. Erythropoietin has a tendency to form aggregates upon storage, and this tendency is accelerated at higher temperatures, as discussed in the DePaolis et. al. article cited earlier. This tendency to form aggregates can be reduced by the proper use of stability enhancers, such as HSA, detergents, and other molecules. The American version of Eprex contained HSA as a stabilizer, and had a good safety track record. The European Union objects to HSA, however, and in 1998, the European version of Eprex was changed to an HSA-free formulation. Within a few months, an unusually large number of red cell aplasia cases were noted in European Eprex users. This disorder, which can result in a complete cessation of red cell production, is caused by an autoimmune reaction against the body's own natural form of erythropoietin.

The reformulated form of Eprex had a higher tendency to form potentially immunogenic aggregates upon exposure to higher temperatures. In an attempt to address this situation, the manufacturer made a point of instructing users that although the product could be safely stored at 4-8° C. for up to 24 months, it should not be kept at room temperature (25° C.) for more than one hour. By contrast, other forms of erythropoietin were capable of being stored for up to 5 days at room temperature (25° C.) without undue chemical change, aggregation, or denaturation. Thus, in this situation, immunological concerns, coupled with the known physical and chemical changes associated with the reformulated product at various temperatures, forced a major stability derating. Due to the lack of appropriate technology to address the situation, however, this derating could only be addressed by a labeling change.

Although changing the labeling to require more stringent temperature handling precautions was a sensible response to the Eprex immunogenicity problem, this change placed a considerable burden on the users of the product. Without suitable monitoring technology, professional healthcare workers could not easily determine if the product had ever received a cumulative temperature exposure of more than one hour at room temperature. Home users, who typically transport and store the product under less than optimal conditions, were particularly disadvantaged by these stringent handling precautions. Indeed, the revised labeling advised against home use.

Example 4 shows how the electronic time-temperature indicator technology of the copending patent Ser. No. 10/634, 297 can assist in managing this type of situation. In this example, the comparative erythropoietin stability data obtained from Anton Haselbeck, "*Epoetins: differences and their relevance to immunogenicity*", Current Medical Research and Opinions 19(5), p 430-432 (2003), is used to provide input data useful for programming a programmable electronic time-temperature indicator that can warn users when a container of erythropoietin has had a potentially immunologically dangerous thermal history.

A table summarizing Haselbeck's comparative stability data on two different forms of Erythropoietin is shown below:

TABLE 1

Storage life of two different erythropoietin drugs

| | Temperature | | | |
|---|---|---|---|---|
| | <0° C. | 4-8° C. (6° C. Avg.) | 25° C. | Denaturation temp |
| Eprex (no HSA) | 0 | 24 months | 1 hour | 53° C.* |
| NeoRecormon | 0 | 36 months | 5 days | 53° C.* |

*Arakawa et. al., Biosci Biotechnology Biochem 65 (6) 1321-1327 (2001)

Eprex (no HSA) is the form of erythropoietin that has a history of generating unwanted immunological reactions. Neorecormon is an alternative form of erythropoietin, produced by a different manufacturer, which has an excellent immunological safety record.

Note that neither form of erythropoietin tolerates freezing, and both have stability data that can be fit by two different Arrhenius plot equations, one covering the range from 1° C. to 25° C., and the other covering the range from 25° C. to 53° C. Neither form of erythropoietin tolerates temperatures above 53° C.

Arrhenius plots: As a brief review, Arrhenius plots are often used to model thermal stability. This type of analysis makes use of the fact that temperature activated reactions, which lie at the heart of thermal stability, are an exponential function of temperature. Thus when the logarithm of product life is plotted versus 1/temperature, the result is typically a straight line, at least over a limited range of temperatures. The slope and intercept of this line can be used to predict the material's stability at various temperatures. Since often, different decay mechanisms are involved at different temperatures, it is helpful to use a series of different Arrhenius equations, each operating over a different temperature domain, as a more accurate way to model a material's stability. This approach is used in this example.

Using Arrhenius log scale techniques, if $\ln(\text{lifetime}) = a + b(1/t)$ (where t is the temperature in degrees Kelvin), then lifetime=$e^{a} \cdot e^{b/t}$.

Note that the use of Arrhenius plots and equations is not necessarily required, or even preferred. Ideally, a large amount of experimental data is obtained, and an empirical "best fit" curve will be used. However in the absence of large amounts of detailed experimental data, Arrhenius plots and equations have a good track record of accuracy. Thus they will be used in this example.

In this example, the two Erythropoietin drugs are each modeled by four equations, which together cover the temperature range from −20° C. to 70° C. This range represents the minimum and maximum temperatures that the drugs would ever be likely to encounter in the field. These four equations are:

For storage temperature<0° C., storage life=0 hours.     Equation 1

For storage temperature>0° C. and <=25° C., storage life=$ae^{-b/(T+273)}$,     Equation 2 where "a" and "b" are coefficients designed to fit the observed stability of the drug in this temperature range using the 6° C. (which is the average of 4° C. and 8° C.) and the 25° C. data points, and "T" represents temperature in degrees centigrade. Here the "273" represents the conversion factor (actually 273.15) needed to convert degrees centigrade into degrees Kelvin, which is needed to properly fit the Arrhenius plot.

For storage temperature>25° C. and <=denaturation temp., storage life=$ce^{-d/(T+273)}$     Equation 3 where "c" and "d" are coefficients designed to fit the observed stability of the drug between its non-zero storage life at 25° C., and its zero storage life at the observed denaturation temperature (53° C.), using the 25° C. and 53° C. data points.

For storage temperature>denaturation temperature (53° C.), storage life=0 hours.     Equation 4

The data from table 1 is fit with an Arrhenius temperature stability model. The equations giving the calculated lifetimes (in hours) of these two drugs as a function of storage temperature (° C.) are shown in table 2 below.

TABLE 2

Lifetime (hours) of Eprex (no HSA) and Neorecormon forms of EPO

| | Temperature | | | |
|---|---|---|---|---|
| | <0° C. | 1-25° C. | 25-53° C. | >53° C. |
| Eprex (no HSA) | 0 | $4.50 * 10^{-63} * e^{42802/(t+273)}$ | $1.14 * 10^{-35} * e^{23990/(t+273)}$ | 0 |
| NeoRecormon | 0 | $4.93 * 10^{-33} * e^{23607/(t+273)}$ | $8.42 * 10^{-58} * e^{40617/(t+273)}$ | 0 |

The Arrhenius plot calculations show that at the point of maximum stability (1° C.), Eprex has a calculated lifetime of 11,962 days, and Neorecormon has a calculated lifetime of 5,120 days. This paradoxical effect (the higher stability Neorecormon has a lower extrapolated 1° C. shelf-life) is probably not real, and is most likely a mathematical artifact caused by the sharp fall in Eprex stability as a function of temperature between 6° C. and 25° C. In practice, this artifact would need to be corrected by incorporating additional experimental data into the model. For these calculations, which are primarily concerned with the region between 6° C. and 53° C., the artifact is minor, and thus the equations will be used as-is.

Using this data, a time-temperature indicator, suitable for warning when the no HSA Eprex has exceeded its recommended thermal profile, can be programmed as originally discussed in copending patent Ser. No. 10/634,297. This process is reviewed below:

To briefly review, copending application Ser. No. 10/634, 297 teaches time-temperature monitors that electronically monitor temperature and compute shelf-life, using microprocessors and visual displays that continually compute shelf life using equations of the type:

$$B = F - \sum_{0}^{Time} P(temp),$$     (Equation 1)

Every few minutes, the device samples the temperature, computes equation 1, and makes an assessment as to if the thermal history has been acceptable or not. Here "B" is the number of points remaining in the units electronic "stability bank", "F" is the initial number of stability points when the product is fresh, and P(temp) is the number of stability points withdrawn from the stability bank each time interval. P(temp) is a function of temperature designed to mimic the product's observed temperature sensitivity. As long as B is greater than zero, the device will display a "+" reading, letting the user know that the drug's stability history has been acceptable. However if B becomes zero or negative, the device will display a "−", indicating that the thermal history is unacceptable.

Using Eprex as an example, the calculations necessary to program the unit to perform equation 1 are shown below.

At the point of maximum stability (1° C.), Eprex has a fresh lifetime "F" of 11,962 days or 287,088 hours. Thus, in this example, assuming that the electronic time-temperature monitor samples the temperature every 6 minutes (1/10 hours), this would be 2,870,879 (6-minute) time units. Since the time-temperature indicators of copending application Ser. No. 10/634,297 use digital arithmetic, to avoid the use of decimal points for the P(temp) values, this stability number "F" will be multiplied by 10 give sufficient resolution to the subsequent integer-based P(temp) values.

Thus, assuming that the temperature is measured every 6 minutes (1/10 hour), and that the minimum P(temp) value is 10, then F=number of time units at the maximum stability temperature=28,708,793 time units.

So the stability bank "B" for fresh Eprex will have an initial deposit of "F" (28,708,793) units (the equivalent calculations with Neorecormin would result in an initial "F" value of 12,287,123 units). Moreover, if the Eprex is kept at a constant 1° C. temperature, P(temp$_{1C}$) should deduct 10 points per hour from the stability bank "B", and the stability equation (1) would be:

$$B = F - \sum_{0}^{Time} P(temp_{1c}) \text{ thus:} \quad \text{(Equation 2)}$$

$$B = 28708793 - \sum_{0}^{Time} 10 \text{ or equivalently,}$$

$$B = 28{,}709{,}793 - Time * 10$$

Where again, Time is a multiple of 6 minutes (1/10 hour).

To determine the P(temp) values for temperatures above 1° C., the experimental stability lifetime data is modeled by the best-fit equations from Table 2. As an example, for the region between 1° C. and 25° C., for Eprex, the stability lifetime calculation is:

$$\text{Stability\_lifetime(hours)} = 4.50 \times 10^{-63} * e^{42802/(temp+273)} \quad \text{(Equation 3)}$$

where "temp" is the temperature in ° C.

To determine the P(temp) values for various temperatures, which is required to program the electronic time-temperature indicators of copending application Ser. No. 10/634,297, it is important to note that at a constant temperature, temp$_c$, equation (1) becomes:

$$B = F - P(temp_c) T \quad \text{(Equation 4)}$$

where "T" is the number of time units.

Now by definition, the stability lifetime is the time "T" when the stability bank "B" first hits zero, so at the stability lifetime limit where B=0, equation (4) becomes:

$$0 = F - P(temp_c) T \text{ so solving for } P(temp_c), \text{ then} \quad \text{(Equation 5)}$$

$$P(temp_c) = \frac{F}{T} \quad \text{(Equation 6)}$$

Thus for any given temperature, P(temp$_c$) is equivalent to the lifetime of the material "F" at the maximum stability temperature, divided by the calculated lifetime of the material at the particular given temperature (temp$_c$).

In this Eprex stability example; the experimental data from table 1, the maximum stability lifetime "F" of 28,708,793, and the best fit stability lifetime from table 2, can be combined with equation (6) to produce a table of P(temp) values, with a temperature granularity of 1° C., that covers the full temperature range between 1° C. and 25° C. In a similar manner, the data between 25° C. and 53° C. can be fit by a second set of calculations. The data <0° C., and >53° C., can be fit by a table of constants, where the values of the constants are chosen so as to have the time-temperature unit instantly expire if these temperature values are reached.

These calculations can be used to produce a table of P(temp) values, shown in table 3 below:

TABLE 3

P(temp) calculations for Eprex and Neorecormon stability between −20 to 70° C.

| Temp | Eprex P(temp) | Eprex Lifetime(h) | Neorecormon P(temp) | Neorecormon Lifetime (h) | Notes |
|---|---|---|---|---|---|
| −20 | 28,708,793 | 0.1 | 12,287,123 | 0.1 | |
| −1 | 28,708,793 | 0.1 | 12,287,123 | 0.1 | |
| 0 | 28,708,793 | 0.1 | 12,287,123 | 0.1 | Freezing |
| 1 | 10 | 287087.9 | 10 | 122871.2 | |
| 2 | 18 | 159493.3 | 14 | 87765.2 | |
| 3 | 31 | 92609.0 | 19 | 64669.1 | |
| 4 | 54 | 53164.4 | 25 | 49148.5 | Low Ref. |
| 5 | 94 | 30541.3 | 34 | 36138.6 | |
| 6 | 164 | 17505.4 | 47 | 26142.8 | Ave. Ref. |
| 7 | 283 | 10144.4 | 63 | 19503.4 | |
| 8 | 488 | 5882.9 | 85 | 14455.4 | High Ref. |
| 9 | 837 | 3430.0 | 115 | 10684.5 | |
| 10 | 1,429 | 2009.0 | 154 | 7978.7 | |
| 15 | 19,677 | 145.9 | 656 | 1873.0 | |
| 20 | 245,374 | 11.7 | 2,653 | 463.1 | |
| 25 | 2,609,890 | 1.1 | 10,231 | 120.1 | Room temp |
| 30 | 7,177,198 | 0.4 | 95,993 | 12.8 | |
| 40 | 28,708,793 | 0.1 | 4,095,708 | 0.3 | |

TABLE 3-continued

P(temp) calculations for Eprex and Neorecormon stability between −20 to 70° C.

| Temp | Eprex P(temp) | Eprex Lifetime(h) | Neorecormon P(temp) | Neorecormon Lifetime (h) | Notes |
|---|---|---|---|---|---|
| 50 | 28,708,793 | 0.1 | 12,287,123 | 0.1 | |
| 53 | 28,708,793 | 0.1 | 12,287,123 | 0.1 | Denaturation |
| 70 | 28,708,793 | 0.1 | 12,287,123 | 0.1 | |

To keep the table to a manageable size, suitable for printing, the temperature entries between −2 to −19, 11 to 14, 16 to 19, 21 to 24, and 25 to 29, 31 to 39, 41 to 49, 51-52, and 54 to 69° C. are not shown.

Note that the table defines a relevant temperature monitoring range for this particular protein. In this example, temperatures that are very outside the range of temperatures expected to be encountered during normal problems in shipment and storage are considered to be non-relevant. Thus, for example, although a drug designed to be stored at room temperature may be accidentally frozen, it is extremely unlikely that it will be accidentally stored in liquid helium, and thus such an unrealistically extreme cold temperature range would be outside of the normal "relevant" temperature range here. Similarly a drug designed to be stored at room temperature may also be exposed to high temperatures such as 60° C. by accidentally being left on a loading dock in a hot day in the summer, but it is extremely unlikely that it will be subjected to temperatures greater than 200° C., except perhaps in a warehouse fire, in which case the package itself will be clearly damaged. Thus this extreme high temperature would also be outside of the relevant temperature range of the device. In the table 3 example above, the relevant temperature range is −20° C. to 70° C. For a drug that might normally be frozen at −70° C., however, the relevant temperature range may be different, such as −100° C. to 70° C.

Note that the P(temp) values were chosen allow the integrator's mathematical model of the drug's stability to correspond to the actual physical chemical model of the drug's stability, which in turn is based on real experimental data. In a case like this, the function of temperature is said to "approximate" the impact of time and temperature on the structure or chemistry of the therapeutic protein.

In many cases, it may be useful to deviate somewhat from the actual physical chemical data. For example, it may be useful to have the computed P(temp) data indicate a constant stability lifetime over a refrigerated temperature range, such as 2-8° C., because normal refrigerators are not precisely temperature controlled, and users would find stability variations between two formulations kept in two supposedly identical refrigerators to be confusing.

In other cases, it may be useful to set the P(temp) or stability bank "B" value to be somewhat conservative, so that the indicator shows a problem at 80% or 90% (or less of a percentage) of its rated stability life, so as to maintain a margin of error. In yet other cases, it may be desired to have the indicator show a problem when a drug reaches 110%, 120% (or greater percentage) of its stability life, so as to only show a problem when the drug has clearly exceeded its expected stability life. In this case, the P(temp) values and equation are said to "substantially approximate" the impact of time and temperature on the structure or chemistry of the therapeutic protein.

Notice that the mathematics behind this method is similar to integral calculus. Like integral calculus, where an integral sums up a large number of tiny steps, and the smaller the steps are, the more accurate the integral is, here too smaller steps are better (more accurate). That is, the smaller the steps are between the various temperature ranges, and the smaller the intervals of time are between the various time periods, the more accurate the approximation to reality will be. Ideally the temperature "steps" in table 3 will be less than 5° C. per step, preferably 1° C. or less. Ideally too, the time steps (periods) in table 3 will be less that 2 hours per step, preferably 1-10 minutes or less per step. This ideal of small temperature and small time steps is referred to as "small granularity". That is, when the steps are large, the granularity is large, and the results tend to be less accurate. When the steps are small the granularity is small, and the results tend to be more accurate. Ideally the granularity should be as small as possible.

Figure 4:
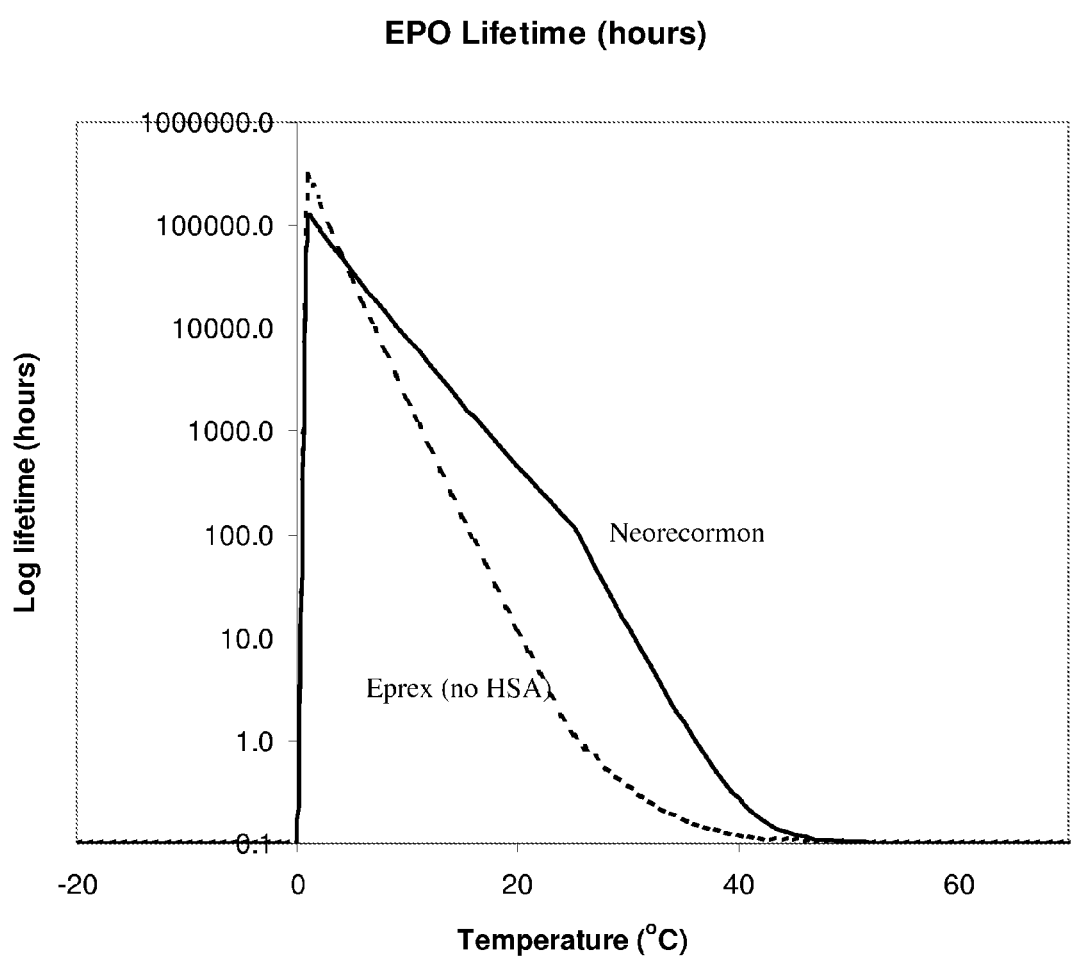
FIG. 4 shows the stability lifetime of Eprex™ and Neorecormon™ forms of erythropoietin.
Figure 5:
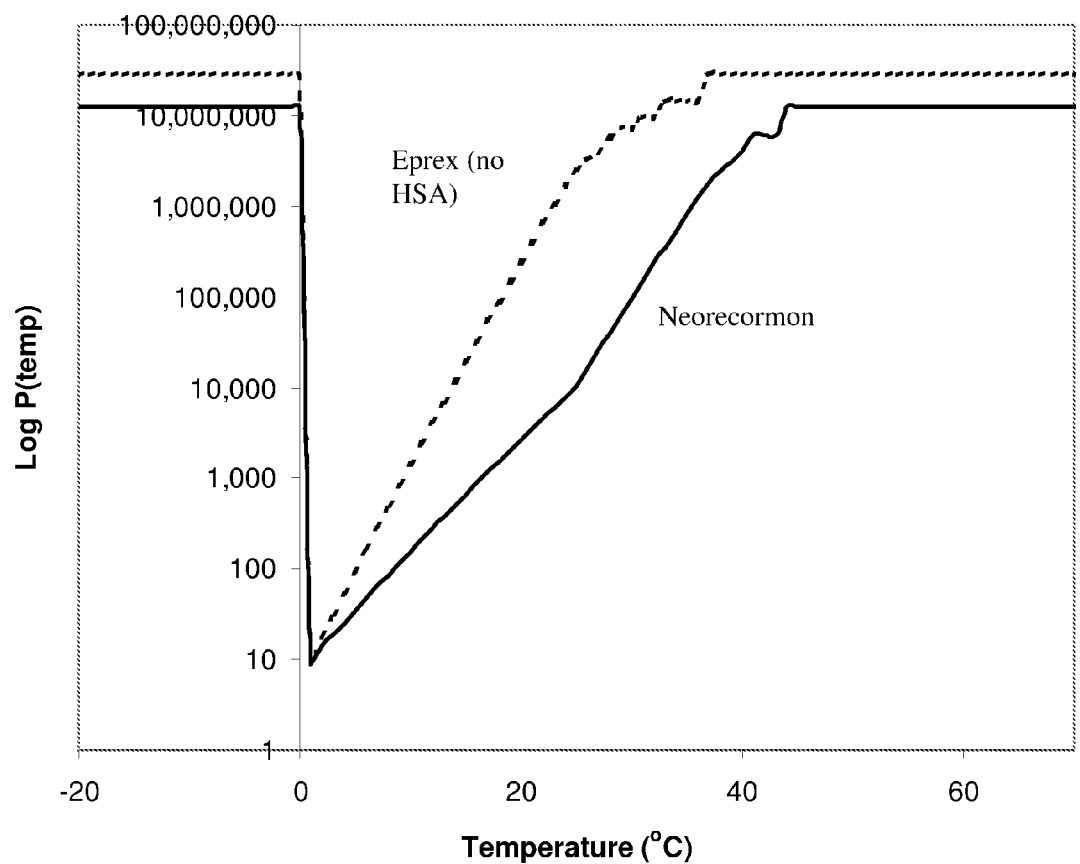
FIG. 5 shows a graph of the coefficients of a time-temperature program designed to mimic the observed functional and immunological stability of Eprex and Neorecormon.

The graphs of comparative Eprex and Neorecormon lifetime as a function of temperature are shown in FIG. 4. The P(temp) values (number of stability points per 6 minutes or 1/10 hour), which is used to program the time-temperature indicators, are shown in FIG. 5.

Time-temperature indicators programmed with this set of P(temp) data can then be included in the no-HSA Eprex packaging, either as an integral part of each container, or as part of a small, multi-container package. Ideally the multi-container is not a large shipping container with hundreds of units, where individual units will be removed and stored at unknown temperatures. Rather, the multi-container should be a small multi-pack, with about 1-20 individual units, so that the individual units will not be removed from the multi-pack, but rather stay with it throughout their storage and use life.

When this configuration is used, the indicator is then able to warn users whenever the thermal-history of the product has exceeded the manufacturer's immunological safety limits. This will help prevent the use of immunologically active degraded material in patients, and thus help reduce the frequency of red cell aplasia.

Figure 6:
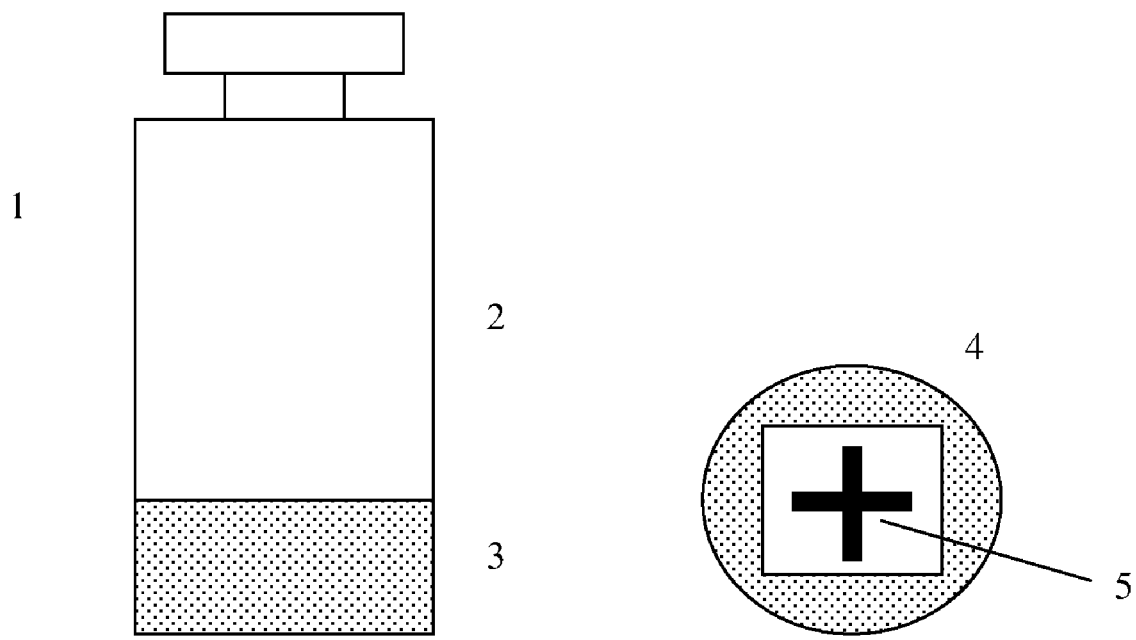
FIG. 6 shows a unitized container-environmental sensor for a therapeutic protein.

FIG. 6 shows an example of a unitized therapeutic protein storage container (1) constructed according to the teachings of the present invention. This storage container consists of a drug storage compartment (2), which may store the therapeutic protein in a lyophilized state, liquid state, or other state. The storage container also contains an environmental monitor (3), such as the electronic time-temperature indicator of Ser. No. 10/634,297; attached to the protein storage compartment so that the indicator and the storage compartment form a unit. This attachment means may be by a permanent link, or by a detachable link, so that the monitor may be reset and reused once the therapeutic protein has been dispensed. If the monitor is affixed by a detachable link, it may be desirable to use a security seal or other mechanism to detect and discourage tampering with the monitor.

The underside of the storage container is shown in (4). In this example, the monitor has a liquid crystal display (5) that shows if the thermal history of the therapeutic protein is acceptable from the immunological standpoint (in which case a "+" is shown), or not acceptable (in which case a "−" is shown).

Figure 7:
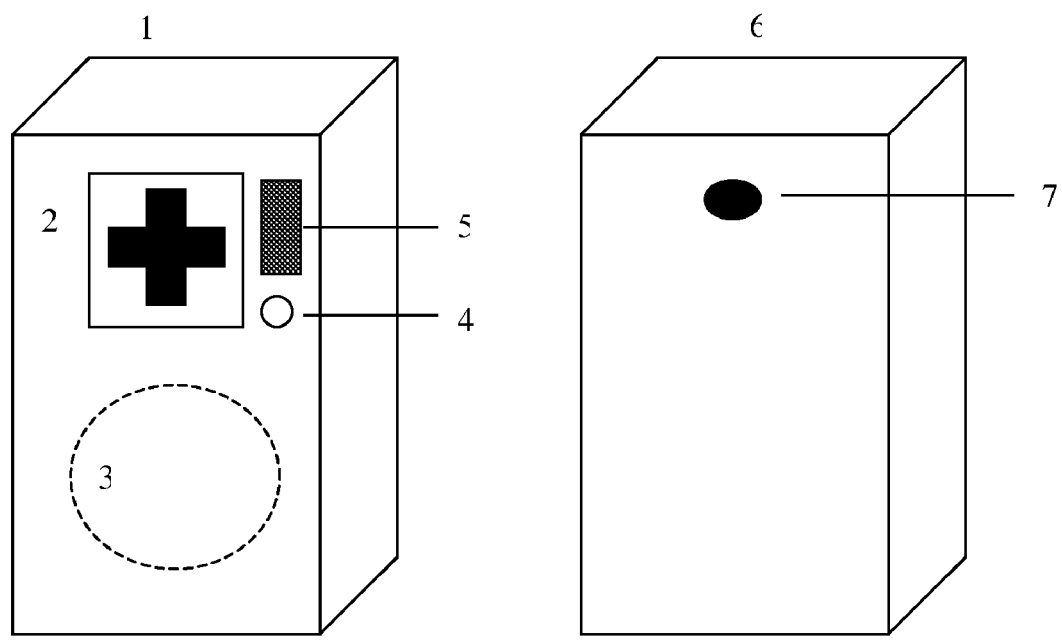
FIG. 7 shows a unitized programmable electronic time-temperature indicator.

FIG. 7 shows an example of a stand-alone time-temperature indicator, suitable for including as part of a multi-pack of multiple storage containers, and designed to comply with relevant Food and Drug Administration (FDA) electronic monitoring requirements. Here, the circuitry is enclosed in case (1) which has a liquid crystal display (2) that displays a "+" symbol if the thermal history of the unit is acceptable (shown), or a "−" if the thermal history is not acceptable (not shown). The unit additionally contains a coin cell battery (3). The front of the unit additionally contains a "data download" button (4), and an infrared (or Radio frequency identification tag—RFID) transmitter (5), so that when the data download button is pressed, relevant statistical information and data validation codes may be transmitted in order to comply with FDA electronic records requirements. The back of the unit, shown in (6) exposes the unit's temperature sensor to the environment inside the multi pack through a temperature sensor mounted on the case surface (7).

Figure 8:
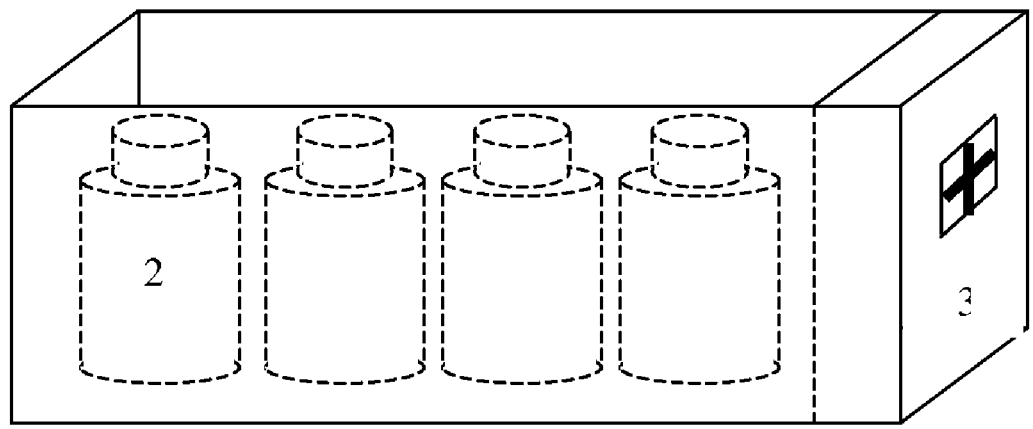
FIG. 8 shows a pharmaceutical container containing an electronic time-temperature indicator.

FIG. 8 shows an example of a multi-pack (1) of pharmaceutical vials (2), containing an electronic time-temperature indicator similar to that of FIG. 7 at one end (3).

Use with Injection Pens

Self-injection devices (autoinjectors, injection pens) allow precise dosages of drugs to be injected by unskilled users in a wide variety of non-clinic environments. These devices are a convenient way to administer biotherapeutic drugs, and are increasingly being used by the pharmaceutical industry for this purpose. However, because self-injection devices are frequently used outside of a normal clinical setting, there is an increased risk that the drugs may accidentally deteriorate due to inadvertent exposure to improper thermal conditions. The safety and effectiveness of drug injection devices can be improved by incorporating time-temperature indicators that monitor drug stability into the injection device.

Self injection devices normally consist of a cartridge where the drug is often (but not always) contained in a fluid state (i.e. usually dissolved in a carrier fluid, such as an aqueous solution), usually a needle for administering the drug, a mechanism that controls the flow of fluid between the cartridge and the needle, and a case, usually made of plastic or metal, that holds the various injector pen components together and allows the user to manipulate the device as a unit.

The drug cartridge can either be permanently mounted in the injection pen, in which case the pen is normally used for a limited number of doses, or alternatively can be replaceable, in which case the pen can be regenerated for further use by replacing the cartridge. The cartridge is a hollow structure, often a cylinder capped at either end, normally be composed of a material such as glass or plastic that is compatible with the drug, and protects the drug from ambient humidity and ambient oxygen.

The dispensing mechanism may either administer the entire contents of the cartridge when a user presses a trigger mechanism attached to the pen, or alternatively dispense a measured subfraction of the amount. Examples of prior art in injection pens include U.S. Pat. Nos. 4,950,246; 5,226,895; 5,334,162; 5,295,976 and many others.

Figure 9:
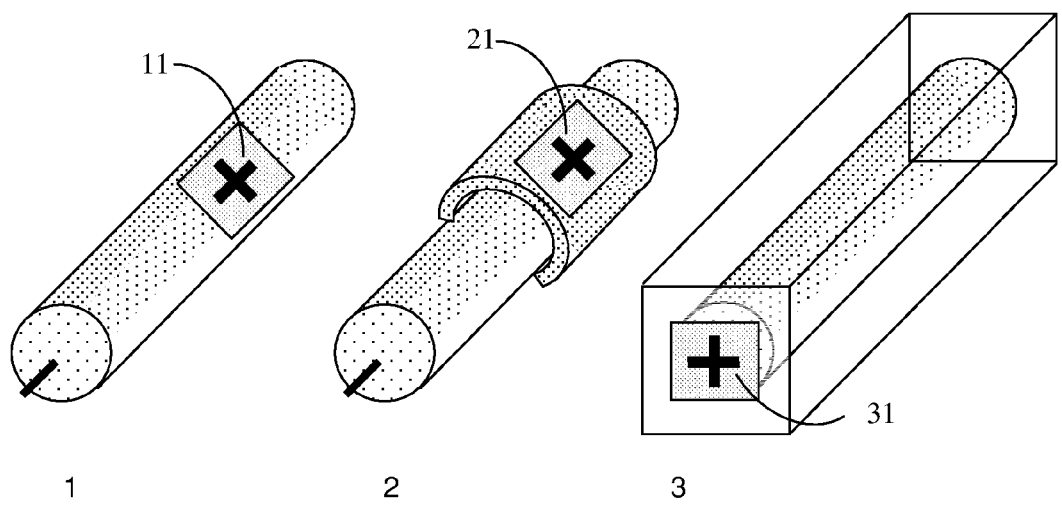
FIG. 9 shows three different ways in which an electronic time-temperature indicator can be used to monitor therapeutic drug stored in a drug injection pen.

FIG. 9 shows three different ways to incorporate time-temperature indicators into injection pens. 1: Time-temperature indicator (11) incorporated as an integral part of the injection pen; 2: Time-temperature indicator (21) incorporated as a clip-on to the injection pen; 3: Time-temperature indicator (31) incorporated as part of the injection pen's external packaging. In cases A and B, the user can instantly assess the drug's fitness for use for the entire use-life of the injection pen. In case C, the user determines if the pen or cartridge is adequate for use before opening the outer packaging.

Various refinements are also possible. The clip-on time-temperature indicator shown in B may be initially stored with the drug cartridge, and then transferred to the injection pen when the drug cartridge is loaded into the pen. Alternatively, the injection pen in A can incorporate a reset switch that resets the time-temperature indicator to "fresh" whenever a new drug cartridge is added.

Often it will be preferable to electronic time-temperature integrators to monitor the stability of therapeutic drugs stored in injection pens, however in some cases, chemical time-temperature indicators may also be used.

In addition to monitoring time-and temperature, in certain cases, it may also be desirable to monitor motion, vibration, ambient light, drug color or drug turbidity as well.

To monitor motion and vibration, it will often be useful to incorporate an electronic acceleration and vibration detector such as a MEMS acceleration sensor chip. It can be important to monitor motion or vibration because some drugs form large light-scattering aggregates, which may present immunological risk, upon excessive shaking or agitation.

Suitable MEMS acceleration chips include dual axis-acceleration and inclination angle measurement systems, such as the Analog devices ADIS16201 programmable dual-axis inclinometer/accelerometer produced by Analog Devices Corporation. Other suitable chips include low-g accelerometer chips, such as the ADXL low-g accelerometer chips, such as the ADXL330, also produced by Analog devices. Such chips detect changes in motion (acceleration). The output from these chips, which represents acceleration, is directed to a microprocessor, which may be the same microprocessor used for the temperature stability calculations. Changes in motion allow the microprocessor to determine if the material that the accelerometer chip is attached to is being shaken. The cumulative degree of changes in motion may be summed up, and this cumulative sum can be used to adjust the stability calculation. Usually shaking will tend to derate a drug's stability according to the equation:

$$B = F - \sum_0^{Time} P(temp_{1c}) - c\sum_0^{Time} accel \qquad \text{Equation 7}$$

Where c is a constant, and "accel" represents changes in motion (acceleration) as reported by the accelerometer. Often the acceleration "accel" value will be further adjusted by a threshold value so that minor changes in motion are ignored, and only major shocks, likely to cause drug denaturation or other damage, are recorded.

Figure 10:
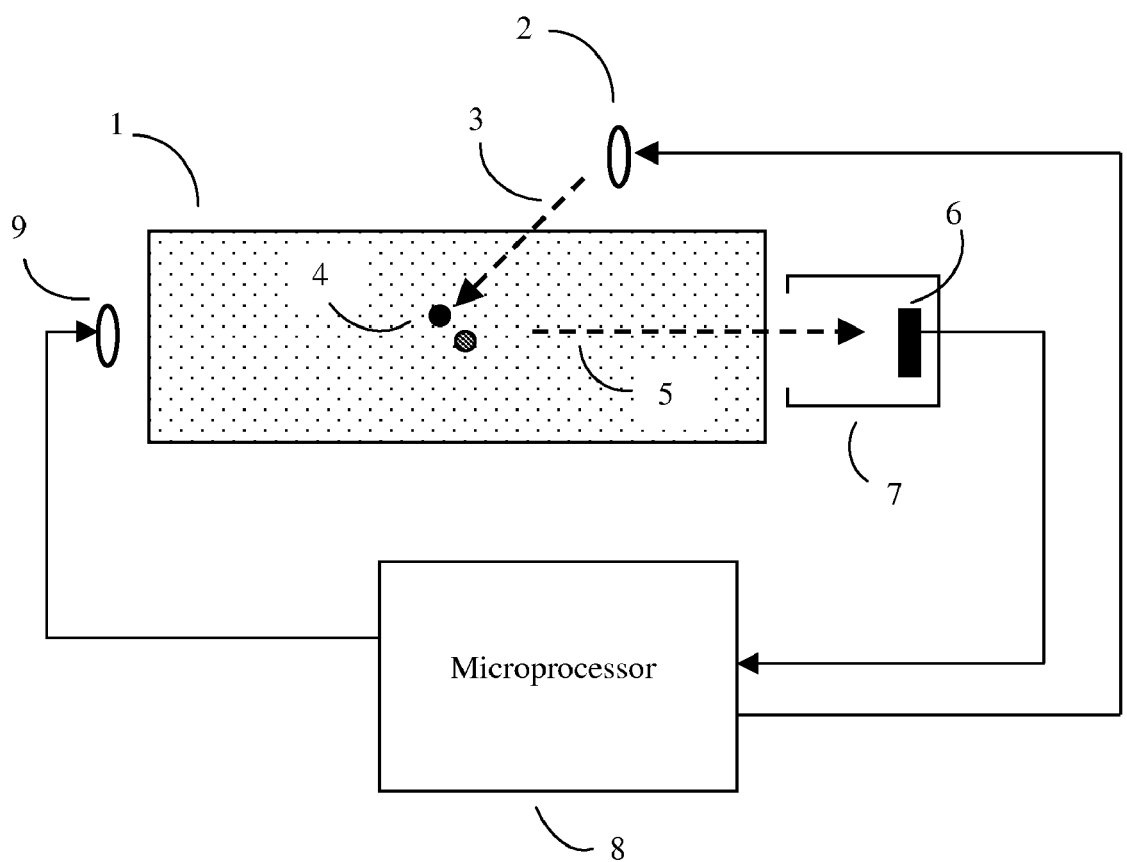
FIG. 10 shows an example of a light, turbidity, and color monitoring circuit.

To monitor ambient light and/or drug turbidity, a simple light-source and photodetector circuit can be used. Many such circuits are known in the art, some of which are exemplified by U.S. Pat. Nos. 3,713,743; 3,809,243; 6,750,966; and others. A diagram of this circuit is shown in FIG. 10. Here the drug, which will typically be dissolved in a liquid, is stored in a container (1). This container will typically be made of glass or plastic, and typically at least a portion of the container walls will contain a light transmissive region. A light source (2), which often will be either a light emitting diode (LED), an incandescent light bulb, or a solid-state laser, will send light into the container (3). If light scattering particles (4) (which often can result when drug deteriorates on storage and forms unwanted aggregates) are present, these particles will scatter light in a different direction (5). The term "turbidity" here, and also as commonly defined, refers to this particle induced light scattering effect.

This scattered light (turbidity) can be detected by a photodectector (6) mounted in a light baffle (7). Light baffle (7) acts to reduce the amount of light going directly from light source (2) to photodectector (6) down to a low level. The geometry of light baffle (7) is such that the main light reaching photodetector (6) is scattered light (5) rather than light directly emitted by the light source (3).

Light source (2) is controlled by microprocessor (8). The output from photodetector (6) is amplified and digitized as needed, and then sent to microprocessor (8). Usually light source (2) and photodetector (6) will be managed by the same microprocessor (8). Microprocessor (8) may be the same microprocessor used to manage the temperature stability calculations, described previously.

Note that photodetector (6) can also be used to measure ambient light (light not originating from photodetector (2)) as desired. Ambient light, more specifically ambient light that hits the drug storage cartridge or container, can be important because some drugs are light sensitive, and either lose activity or form harmful side products upon exposure to excessive ambient light. Thus excessive ambient light can tend to reduce drug stability lifetime.

In order to better distinguish scattered light from ambient light, it often will be advantageous for microprocessor (8) to operate light source (2) in a pulsed on-off mode. In this way, signals originating from photodetector (6) when the light source (2) is off may be used to calculate the amount of ambient light hitting the drug container (1), and the difference between the signal originating from the photodetector (6) when light source (2) is on, minus the signal originating from the photodetector (6) when light source (2) is off, can be used to calculate the amount of light scattering (turbidity) generated by the drug stored in container (1).

With minor modifications, a simple light source-photodetector configuration, similar to FIG. 10, can also be used to detect drug discoloration (drug color). Some drugs, such as epinephrine, discolor or change color upon deterioration. In order to detect this discoloration, an alternate light source (9), which preferably can be switched by microprocessor (8) to emit light at more than one wavelength, can be mounted so that light from (9) travels through an appreciable amount of drug (1) before directly hitting photodiode (6). By looking at the decline in efficiency in light transmission after the drug has deteriorated, and by comparing this with the efficiency of light transmission when the drug was fresh (where the fresh value is ideally stored in a memory accessible to microprocessor (8), then the amount of discoloration of the drug may be determined. Alternatively, the difference in transmission efficiency between a first wavelength of light emitted by light source (9) which is not absorbed by the discolored drug, and the transmission efficiency between a second wavelength of light emitted by light source (9), which is absorbed by the discolored drug, may also be used to compute the amount of drug color change, and hence the amount of drug deterioration.

Examples of suitable multiple wavelength light sources include dual wavelength light emitting diodes (LED's). Examples of such dual wavelength circuits may be found in U.S. Pat. Nos. 5,175,438; 5,307,146; 6,801,799 and others.

As is the case for the previous motion detection example, results from the turbidity detector, ambient light detector, or color change detector can also be used to further adjust the drug's lifetime. Typically all of these effects act to further reduce the drug's lifetime, and thus all effectively subtract from the basic stability bank equation discussed previously. A more comprehensive equation that incorporates all of these effects is shown below:

$$B = F - \sum_{0}^{Time} P(temp_{1c}) - c\sum_{0}^{Time} accel - d(turbidity) - e(discoloration) - f\sum_{0}^{time} ambient \qquad \text{Equation 8}$$

here "accel" is the amount of observed acceleration, "turbidity" is the amount of turbidity detected by the turbidity detector, "discoloration" is the amount of discoloration detected by the discoloration detector, and "ambient" is the amount of ambient light recorded by the photodiode (FIG. 10(6)) when the light sources (FIG. 10(2) and FIG. 10(9)) are off.

In equation 8, "c" is a constant that relates the cumulative observed acceleration to a quantitative decrease in drug stability, "d" is a constant that relates the observed turbidity to a quantitative decrease in drug stability, "e" is a constant that relates the observed drug discoloration to a quantitative decrease in drug stability, and "f" is a constant that relates the cumulative ambient light exposure to a quantitative decrease in drug stability.

The detection circuit of FIG. 10 may be used in various configurations. It may be embedded into the time-temperature monitor shown in FIG. 6(4), and used to monitor a drug vial. Alternatively it may be used with the injection pen configurations shown in FIG. 9, and either embedded into the injection pen itself (FIG. 9(1), or used as a clip-on to the injection pen (FIGS. 9(2) and 9(21)). Although to get a clear signal, the device will normally be placed right up against the drug storage container, rather than being placed separate from the container in a different part of the packaging, if the characteristics of the drug storage container and the packaging permit a good optical observation of the drug, the detection circuit may also be placed as part of the drug's outer packaging, as is shown in FIG. 9(3).

The invention claimed is:
1. A method for monitoring a therapeutic protein drug for immunological risk, said method comprising;
providing a time-temperature integrator indicator device to integrate time and temperature, an indicator output device, and a time-temperature indication parameter setting device;
said indicator having at least one time-temperature indication parameter selected by the steps of:
monitoring chemical and structural changes in the therapeutic protein as a function of time and storage temperature;
determining which time and temperature conditions cause a certain percentage of said protein to undergo structural or chemical alterations;
said percentage being set at a predetermined immunological risk threshold wherein amounts above said threshold have an unacceptable risk of provoking an immunological reaction;
in which it is unwanted that said therapeutic protein drug provoke an immunological reaction in the absence of said structural or chemical alterations, and in which said therapeutic protein drug is not a vaccine;
said immunological risk threshold being set at or below ten percent of the total quantity of said therapeutic protein;

setting said time-temperature indication parameter of said indicator with said immunological risk time-temperature data;

associating said immunological risk set indicator with said drug throughout the cold chain or distribution chain between the manufacturer and the ultimate end user so as to detect disruptions in said cold chain or distribution chain during the drug's storage life;

and monitoring the immunological risk status of said therapeutic drug by observing the indicator output of said time-temperature integrator.

2. The method of claim 1, in which said the time-temperature integrator is selected from the group consisting of chemical time-temperature integrating indicators and electronic time-temperature integrating indicators.

3. The method of claim 1, in which the time-temperature integrator additionally monitors parameters selected from the group consisting of motion, vibration, ambient light, drug color or drug turbidity, and adjusts its immunological risk threshold depending upon said additional parameters.

4. The method of claim 1, in which said therapeutic protein structural changes are selected from the group consisting of protein aggregation, denaturation, dimerization, oxidation, deamidation, disulfide exchange, proteolysis, peptide map change, creation of antigenic activity, creation of antibody epitopes, or destruction of antibody epitopes.

5. The method of claim 1, in which the time-temperature integrator is incorporated into or interfaced with a therapeutic protein dispensing device, in which the time-temperature device signals if the therapeutic protein should be dispensed or not depending upon the acceptability of the material's thermal history.

6. The method of claim 1, in which said therapeutic drug is stored in an injection pen, and said time temperature integrator is associated with said injection pen by methods selected from the group consisting of attachment to said injection pen, embedding in said injection pen, and attaching to packaging materials associated with said injection pen.

7. The method of claim 1, in which said indicator output is selected from the group consisting of visual output signals, vibration output signals, sonic output signals, radiofrequency output signals, RFID tag output signals, electrical output signals, or infra-red output signals.

8. The method of claim 1, in which said time-temperature integrator is a unitized electronic time-temperature integrator that contains a computational device, and a temperature measurement device;

wherein said integrator periodically samples the temperature and computes a function of temperature that is continually operative throughout the relevant temperature monitoring range of the integrator;

and wherein said function of temperature approximates the impact that the relevant temperature, for that period's length of time, has on alterations in the structure or chemistry of said therapeutic protein;

and wherein said computational computing device generates a running sum of said function of temperature over time;

and wherein said function of temperature resides with said unitized device;

and wherein the granularity of the function of temperature is small enough, and the frequency of time measurements is often enough, as to substantially approximate the impact of time and temperature on the alterations in the structure or chemistry of said therapeutic protein;

and in which said running sum is compared to a reference value, and the result of said comparison is used to generate an output signal indicative of the immunological risk status fitness for use of said therapeutic protein;

wherein said relevant temperature is the temperatures expected to be encountered during normal problems in shipment and storage, said that period's length of time is two hours or less, said small enough is a function of temperature with a granularity of 5° C. or less, and said often enough is a frequency of time measurements of every 2 hours or less;

and wherein said period's length of time is 10 minutes or less, said small enough is a function of temperature with a granularity of 1° C. or less, and said often enough is a frequency of time measurements of every 10 minutes or less.

9. The method of claim 8, in which the time temperature integrator further contains a device to enable the time-temperature indication parameters to be automatically programmed into the assembled integrator.

10. The method of claim 8, in which the time-temperature integrator is controlled by a microprocessor, the microprocessor is continually powered throughout its use lifetime, and the power source is selected from the group consisting of battery, storage capacitor, thermal, photoelectric, AC power, or radio frequency energy.

11. The method of claim 8, in which the time-temperature integrator additionally conveys information selected from the group consisting of thermal history statistics, percentage of remaining lifetime, identification codes, and therapeutic protein prescribing information.

12. The method of claim 1, in which said immunological risk threshold is determined by a method comprising: constructing a pool of antibody or immune response genes representative of the genetic diversity of a target population;

using said genetic pool to produce a panel of antibodies or immune response proteins directed against one or more representative samples of said therapeutic protein, using said panel to determine which epitopes are expressed on various preparations of said therapeutic proteins under various storage conditions;

said storage conditions representing at least different combinations of time and temperature storage parameters;

and determining what combinations of time and temperature storage parameters are associated with the formation of epitopes representative of immunogenic risk.

13. The method of claim 12, in which the panel of antibodies or immune response proteins is produced using methods selected from the group consisting of phage display, ribosome display, or lymphocyte antibody production methods.

14. A method for monitoring a therapeutic protein stored in an injection pen for immunological risk, said method comprising;

associating said injection pen with a time-temperature integrator indicator device that integrates time and temperature, an indicator output device, and a time-temperature integration parameter setting device;

said indicator having at least one time-temperature integration parameter selected by the steps of:

monitoring chemical and structural changes in the therapeutic protein as a function of time and storage temperature;

determining which time and temperature conditions cause a certain percentage of said protein to undergo structural or chemical alterations;

said percentage being set at a predetermined immunological risk threshold wherein amounts above said threshold have an unacceptable risk of provoking an immunological reaction;

in which it is unwanted that said therapeutic protein drug provoke an immunological reaction in the absence of said structural or chemical alterations, and in which said therapeutic protein drug is not a vaccine;

said immunological risk threshold being set at or below ten percent of the total quantity of said therapeutic protein;

setting said time-temperature indication parameter of said integrator with said immunological risk time-temperature data;

associating said immunological risk set indicator with said drug and said injection pen throughout the cold chain or distribution chain between the manufacturer and the ultimate end user so as to detect disruptions in said cold chain or distribution chain during the drug's storage life;

and monitoring the immunological risk status of said therapeutic drug by observing the indicator output of said time-temperature integrator.

15. The method of claim 14, in which the time-temperature integration indicator additionally monitors parameters selected from the group consisting of motion, vibration, ambient light, drug color or drug turbidity, and adjusts its immunological risk threshold depending upon said additional parameters.

16. The method of claim 14, in which said time temperature integrator is associated with said injection pen by methods selected from the group consisting of a clip-on attachment to said injection pen, an adhesive attachment to said injection pen, embedding in said injection pen, and attaching to packaging materials associated with said injection pen.

17. The method of claim 14, in which the time-temperature indicator is controlled by a microprocessor, the microprocessor is continually powered throughout its use lifetime, and the power source is selected from the group consisting of battery, storage capacitor, thermal, photoelectric, AC power, or radio frequency energy.

* * * * *